United States Patent [19]
Ortiz et al.

[11] Patent Number: 5,346,504
[45] Date of Patent: Sep. 13, 1994

[54] INTRALUMINAL MANIPULATOR WITH A HEAD HAVING ARTICULATING LINKS

[75] Inventors: Mark Ortiz, Milford; Joseph Paraschac, Cincinnati, both of Ohio

[73] Assignee: Ethicon, Inc., Somerville, N.J.

[21] Appl. No.: 979,501

[22] Filed: Nov. 19, 1992

[51] Int. Cl.⁵ ............................................. A61B 1/26
[52] U.S. Cl. ................................. 606/192; 128/6; 128/10; 128/18; 128/20
[58] Field of Search .................... 128/4, 6, 17, 10, 20, 128/18; 604/95, 96, 105–109; 606/1, 110, 113, 190–194, 196, 198

[56] References Cited

U.S. PATENT DOCUMENTS

| | | | |
|---|---|---|---|
| 1,606,498 | 11/1926 | Berger | 606/110 |
| 3,091,235 | 5/1963 | Richards | 128/6 |
| 4,203,430 | 5/1980 | Takahashi | 128/4 |
| 4,290,421 | 9/1981 | Siegmund | 128/6 |
| 4,401,123 | 8/1983 | Baba | 128/6 |
| 4,832,473 | 5/1989 | Ueda | 128/6 |
| 4,841,950 | 6/1989 | Fukuda | 128/4 |
| 4,996,974 | 3/1991 | Ciarlei | 128/4 |
| 5,152,277 | 10/1992 | Honda et al. | 128/4 |
| 5,158,086 | 10/1992 | Brown et al. | 128/4 |

*Primary Examiner*—Stephen C. Pellegrino
*Assistant Examiner*—Glenn K. Dawson
*Attorney, Agent, or Firm*—Paul A. Coletti

[57] ABSTRACT

The present invention is directed towards an intraluminal manipulator which extends into a lumen and is operable to position and manipulate the tissue surrounding the lumen as necessary during a medical procedure. The manipulator includes a head, a handle and an interconnecting shaft. A pair of cables extend through the shaft and interconnect the head and handle. Movement of a trigger provided by the handle moves the head, which is formed by a series of articulated links, between generally straight and arched configurations. Movement of the trigger in one direction moves the head from a straightened to an arched configuration, while movement in an opposite direction moves the head from the arched to the straightened configuration. When placed in the straight configuration, the head is insertable into and removable from the lumen. When the head is in the arched configuration, it engages the walls surrounding and defining the lumen and can thereafter be used to manipulate the tissue. A fiber optic bundle is provided to allow remote visualization of the lumen, and an expandable balloon is used to provide a better frictional engagement between the head and the tissue defining the lumen.

28 Claims, 6 Drawing Sheets

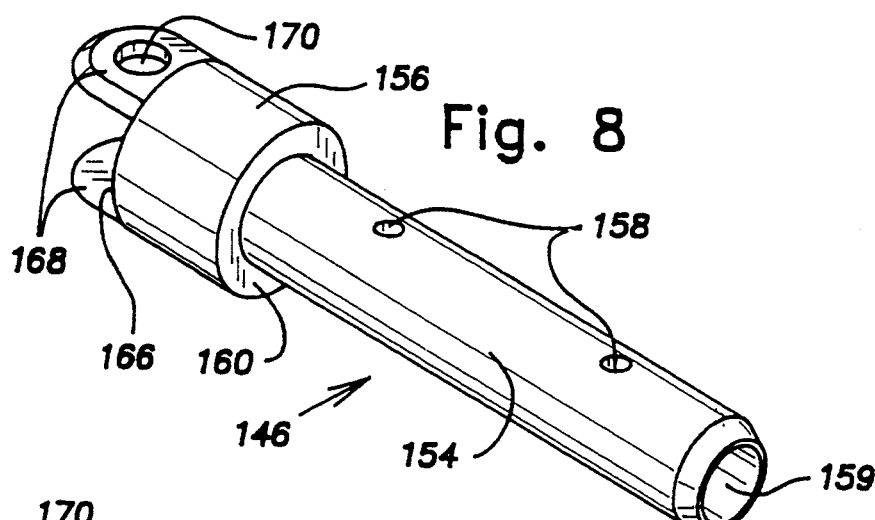
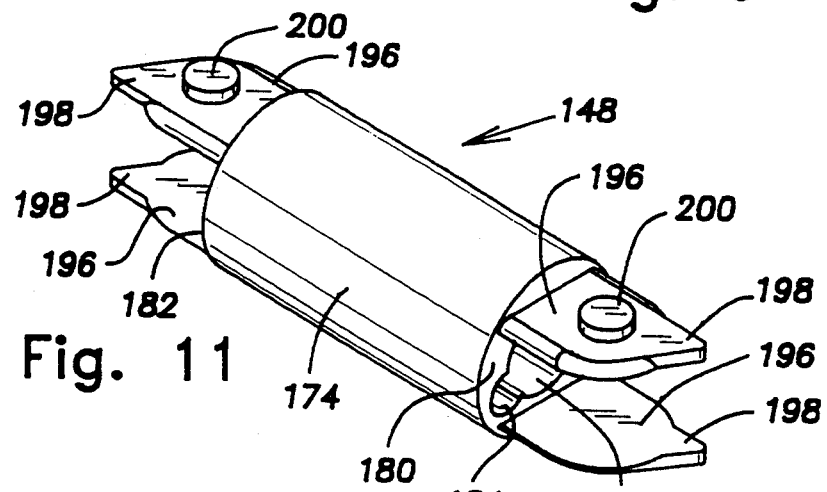
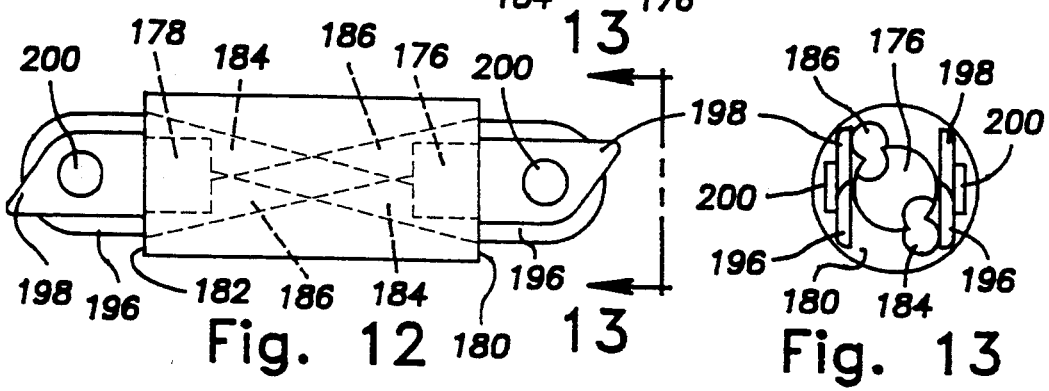

INTRALUMINAL MANIPULATOR WITH A HEAD HAVING ARTICULATING LINKS

BACKGROUND OF THE INVENTION

1. Field of the Invention

The present invention is generally directed towards a device which is used to reposition tissue within a body and, more particularly, to an intraluminal manipulator which is operable to extend into a lumen and engage and reorient the tissue which defines the lumen.

2. Description of the Related Art

During surgical procedures it is sometimes necessary to move or otherwise reorient certain tissues. With regard to the esophagus, such reorientation is typically accomplished by the surgeon directly engaging the exterior of the esophagus either with his hands or with tools specially developed for that purpose. The esophagus is thereafter restrained to prevent it from returning to its normal position until the procedure is finished.

However, due to spatial constraints, it is often inconvenient or difficult for the surgeon to manipulate the esophagus or other tissues from the exterior thereof. Moreover, in modern microsurgery or endoscopic surgery the tissues to be reoriented are typically not exposed. With conventional manipulation techniques it is necessary to expose the tissue, creating additional trauma and prolonged hospital stays for the patient along with an increased risk of infection.

Therefore, there exists a need in the art for a device which extends into a lumen and allows the surgeon to manipulate and restrain the tissue therearound during a medical procedure. There also exists a need in the art for a device which manipulates the lumen-defining tissue in a manner not requiring surgical exposure thereof.

SUMMARY OF THE INVENTION

The present invention is directed towards an intraluminal manipulator which does not require surgical exposure of the tissue into which it extends and which is selectively operable to lift, rotate, axially translate and reposition the tissue during a medical procedure, such as Nissen fundoplications, vagotomies, esophagectomies, and other procedures. In accordance with one use of the invention, the manipulator is inserted into the patient's esophagus, and is thereafter used to place the esophagus in a desired position.

The intraluminal manipulator of the present invention includes head, shaft and handle portions. The shaft extends between and interconnects the head and the handle. In keeping with the present invention, the handle is operable to control movement of the head and, consequently, manipulation of the tissue surrounding the lumen into which the head is placed.

The handle includes a body portion having first and second sections, a pawl, and a trigger. The first and second body sections matingly define an inner chamber and a central aperture. One of the body sections provides a pair of ratchets which are engaged by the pawl. The pawl and the trigger are received within the inner chamber, the trigger including an outer end which extends through the first and second body sections into the central aperture.

In further accordance with the present invention, the pawl includes front and rear paired legs, an upstanding section and a central body section. The central body section includes a pair of upstanding rails which are received by slotted openings in an inner end of the trigger. The inner end of the trigger further includes a pair of raised slides which are operable to disengage paired legs of the pawl from the ratchets. The rails are engaged by the trigger after the legs are disengaged from the ratchets, thereby forcing the pawl to move with the trigger within the inner chamber.

The head includes a series of articulated links. One of the links, an adaptor link, is attached on one end to a terminal end of the shaft and, on another end, to an angle link. The angle link extends between, and is pivotally attached to, the adaptor link and a tip link. Stop means are provided on the adaptor link and the tip link to limit the relative angular range of pivot of the angle link. A terminal end of the tip link has attached thereto a nose tip which optionally carries a light source to facilitate viewing of the position of the manipulator from an exterior of the body. A thin, flexible elastomeric sheath covers the head and shaft to facilitate insertion of the manipulator into the body, and to avoid pinching of tissue around the head.

Extending between and interconnecting the head and the handle is a multi-lumen shaft. The shaft carries arching and straightening control cables, a fluid communicating tube, and a fiber optic bundle. The control cables extend from the tip link to the pawl, the straightening cable directly connecting to the upstanding section of the pawl while the arching cable first passes around a rib carried by one of the body sections before attaching to the upstanding section. At the head, the arching and straightening cables take individual routes through the links to allow the head to bend and straighten in a predetermined direction and manner. The fluid communicating tube includes a connector which extends through the handle to allow the introduction of pressurized fluid therein.

In accordance with the present invention, movement of the trigger towards a front of the handle causes the head to arch, while movement of the trigger towards a rear of the handle causes the head to straighten. Once the head is arched to engage the sides of the esophagus, rotating, axially translating, and lifting of the manipulator will result in a like movement of the esophagus.

In further accordance with the present invention, an expandable balloon is provided by the head. The balloon, which is in fluid communication via the tube carried by the shaft and handle, is expandable to engage the sidewalls surrounding the lumen in which the manipulator is placed, facilitating the frictional engagement of the head with the lumen walls. A valve means is provided by the handle to control fluid communication with the balloon.

Visualization of the area in front of the head is provided by the fiber optic bundle which extends from the handle to the head via an unused lumen of the shaft. The terminal end of the fiber optic bundle extends through the end of the head, allowing the surgeon to see the interior of the lumen in which the manipulator is placed. The other end of the fiber optic bundle terminates at the handle in a coupling for a fiberscope.

BRIEF DESCRIPTION OF THE DRAWINGS

These and further features of the present invention will be apparent with reference to the following description and drawings, wherein:

FIG. 8 is a perspective view of the head adaptor link of the present invention;

FIG. 9 is a front elevational view of the head adaptor link;

FIG. 10 is a side elevational view of the head adaptor link as seen from line 10—10 of FIG. 9;

FIG. 11 is a perspective view of the head angle link of the present invention;

FIG. 12 is a top plan view of the head angle link;

FIG. 13 is a side elevational view of the head adaptor link as seen from line 13—13 of FIG. 12;

DETAILED DESCRIPTION OF THE PREFERRED EMBODIMENT

Figure 1:
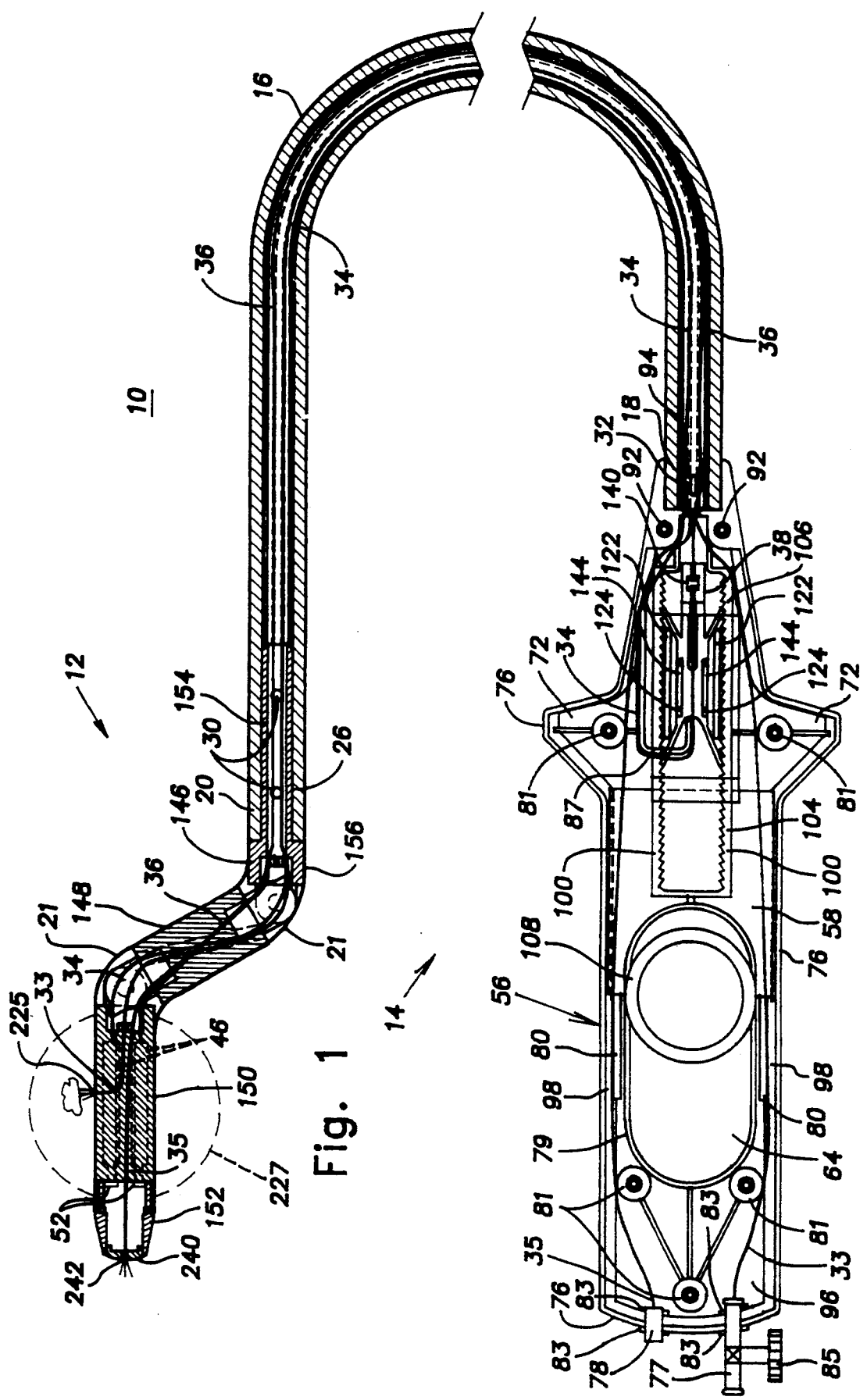
FIG. 1 is a plan view, in cross section, of the present invention.
Figure 2:
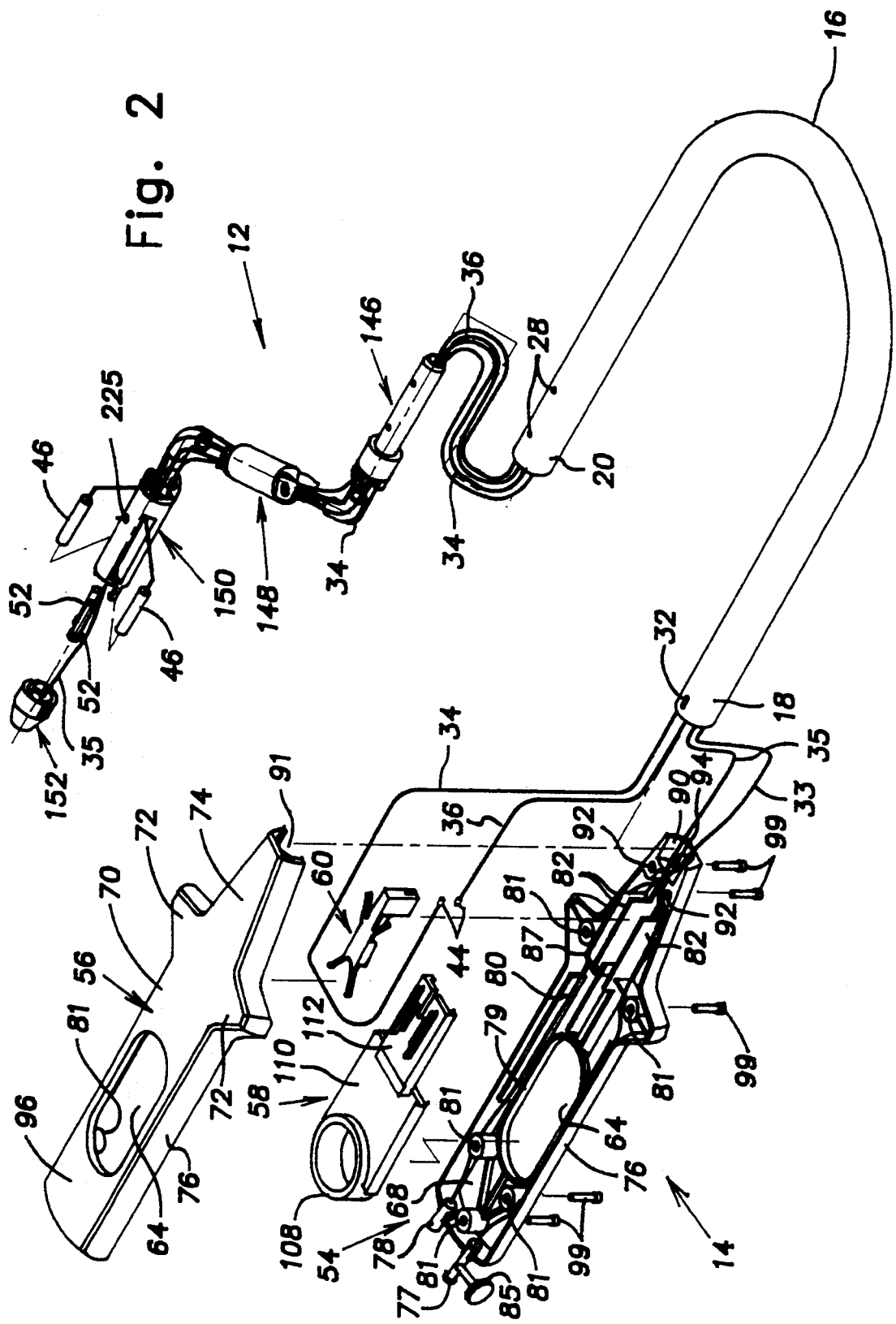
FIG. 2 is an exploded perspective view of the present invention.

With reference to the drawing figures and in particular FIGS. 1 and 2, an intraluminal manipulator 10 of the present invention is shown to generally include a head 12, a handle 14, and a shaft 16.

The shaft includes a proximal end 18 which is adapted to attach to the handle 14 and a distal end 20 which is adapted to attach to the head 12. The head 12 and shaft 16 are preferably covered by a thin, flexible elastomeric sheath 21 (FIG. 1) which facilitates the introduction of the head 12 into a body and helps to prevent the pinching of tissue around the head 12.

Figure 7:
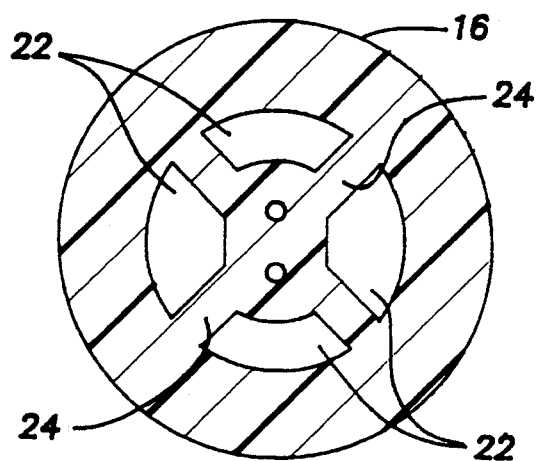
FIG. 7 is a cross-sectional view of the shaft of the present invention.

As shown best in FIG. 7, the shaft 16 provides a plurality of longitudinal inner channels or lumens 22 which are separated by internal walls 24 generally extending the length of the shaft 16. The internal walls 24 terminate a short distance from the distal end 20 of the shaft, allowing the distal end to provide a cylindrical bore 26 which receives the head. A pair of crossbores 28 extend through the sidewall of the distal end 20 of the shaft 16 to communicate with the cylindrical bore 26. The crossbores 28 receive mounting pins 30 to positively mount the head 12 to the shaft 16, as will be more fully described hereafter.

The proximal end 18 of the shaft includes a crossbore 32, which is adapted to receive axially aligned mounting projections from the handle 14. The shaft allows communication between the handle 14 and the head 12 for a pair of cables 34 and 36, a fluid communicating tube 33, and a fiber optic bundle 35, which comprise control means of the present invention. The cables 34 and 36 transfer motion from an actuator carried by the handle 14 to the head 12, as will be clear from the following description. The fluid communicating tube 33 communicates fluid to an expandable member provided by the head, while the fiber optic bundle 35 allows remote visualization of the head position, as will be described more fully hereafter.

In the preferred embodiment, the cables 34 and 36, the fluid communicating tube 33, and the fiber optic bundle 35 are each inserted into one of the longitudinal channels or lumens 22 provided by the shaft 16, as illustrated in FIGS. 1 and 2. As will be apparent from the following description, one of the cables, the arching cable 34, is operable to move the head 12 into an arched or less straight configuration, while the other of the cables, the straightening cable 36, is operable to move the head 12 into a straight or less-arched configuration. The straightening cable 36 extends directly from a mounting post 38 associated with the handle 14 to the head while the arching cable 34 takes a longer route in traveling the distance from the mounting post 38 to the head.

By having each of the cables 34 and 36 extend through individual lumens 22 instead of through a larger common bore, the variations in cable length and, hence, head configuration, caused by bending or otherwise repositioning the shaft 16 are minimized. The cables 34 and 36 also travel different routes within the head 12 to facilitate arching and straightening thereof, as will be apparent from the following description.

Figure 18:
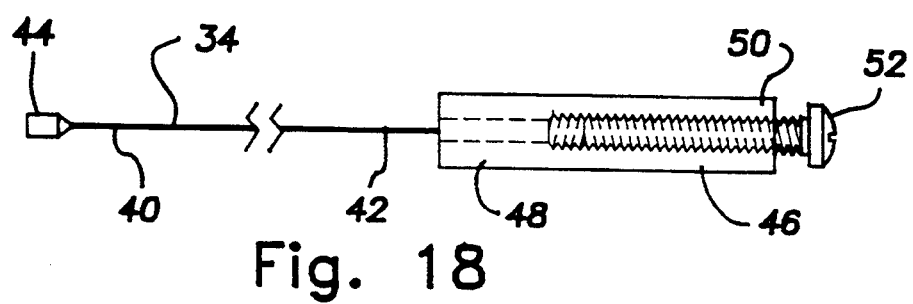
FIG. 18 is a plane view, with portions broken away, of the arching cable and a turnbuckle of the present invention.

Each cable 34 and 36 includes identical mounting arrangements. For purposes of simplicity, the mounting arrangement associated with cable 34 is illustrated in FIG. 18. The cable 34 includes a proximal end 40 which is received by the mounting post 38 of the handle and a distal end 42 which is received by the head 12. The proximal end 40 of the cable includes a terminal knob or ball 44 which serves as a stop or retention means to prevent removal of the cable 34 from the mounting post 38. The distal end 42 of the cable 34 is attached to a turnbuckle 46 which is operable to tension the cable and prevent removal of the same from the head 12.

As will be described more fully hereafter, the turnbuckle 46 is received by the head 12 and includes a cable-receiving end 48 and a tensioning screw-receiving end 50. A screw 52 is turned to axially move the turnbuckle 46 relative to the head 12, and thereby tension the cable 34. In the present invention, the turnbuckle 46 provides a convenient means to initially establish and adjust the lengths of the straightening 36 and arching cables 34. Also, by providing a turnbuckle, there is some adjustability of lengths should a customized manipulator 10 be necessary for a particular application, i.e. to have the head extend a predetermined distance into the lumen.

With reference to FIGS. 1-6, the components of the handle are particularly shown. The handle 14 includes first and second body sections 54 and 56, a trigger 58, and an X-shaped pawl 60. The first and second body sections 54 and 56 cooperate to form an inner chamber which receives the X-shaped pawl 60 and an inner end 62 of the trigger 58. The body sections further cooperate to define a central aperture 64 (FIG. 1) which receives an outer end 66 of the trigger 58.

Figure 3:
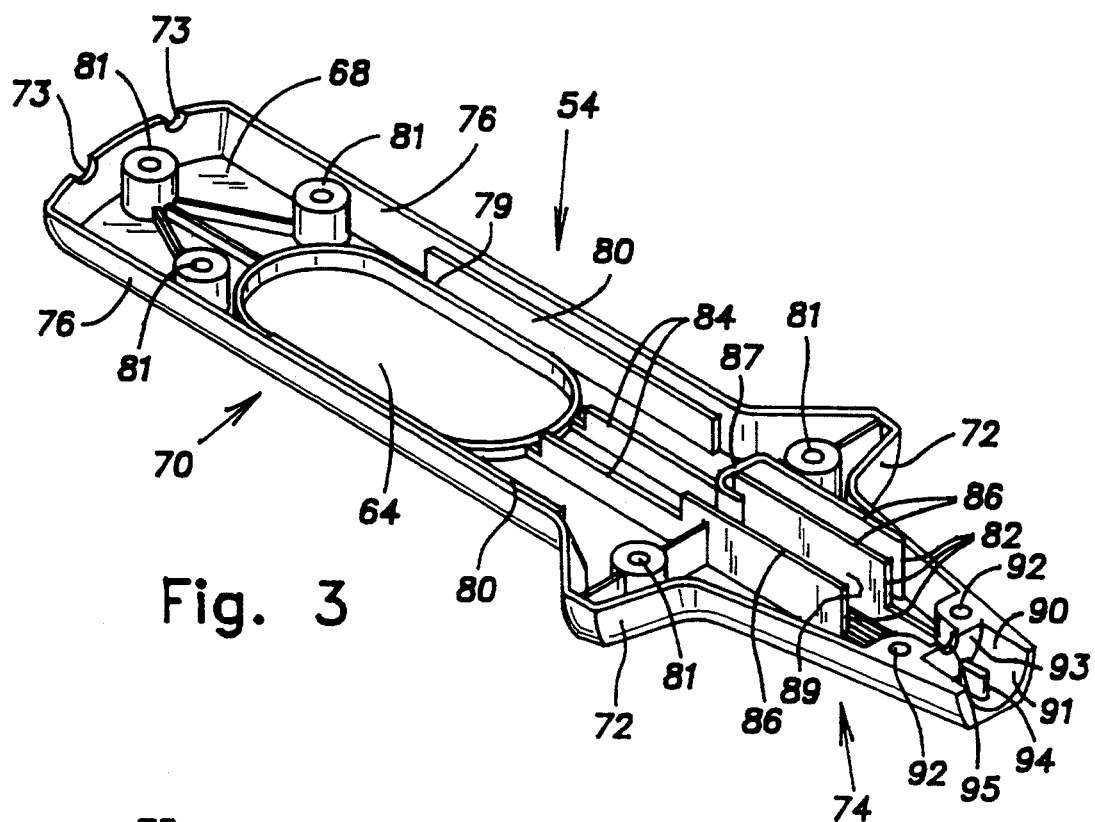
FIG. 3 is a perspective view of the interior of the first body section of the present invention.

With specific reference to FIGS. 2 and 3 wherein the interior of the first body section is shown, the first body section 54 integrally includes a first planar surface 68 which extends between and generally covers a generally rectangular main section 70, a pair of outwardly extending wings 72, and a nose section 74. An outwardly flared raised wall 76 extends from the perimeter of the first planar surface 68, generally surrounding the main section 70, the wings 72 and the nose section 74, as illustrated.

The raised wall 76 of the first body section 54 has formed therein a pair of semi-circular notches 73 which cooperate with like notches 75 in the second body section 56 (FIG. 4) to receive connectors 77, 78 (FIGS. 1 and 2) for the fluid communicating tube 33 and the fiber optic bundles 35, shown in phantom respectively. Each of the connectors 77, 78 includes a pair of raised annular surfaces 83 which engage opposite sides of the raised wall 76 when the first and second body sections 54, 56 are attached, to prevent removal of the connectors 77, 78 from the handle 14. The connector 77 for the fluid communicating tube 33, which is adapted to attach to a conduit (not shown) leading from a pressurized fluid source (not shown) includes a stop cock to control fluid flow through the tube 78. The connector 78 for the bundle of fiber optic cables 35 is adapted to receive a fiberscope (not shown).

At the first planar surface 68, the main section 70 includes the central aperture 64, a pair of raised ribs 80 and a series of raised fastener-receiving bosses 81. The central aperture 64 is surrounded by a raised surface 79 which slidably supports an outer end 66 of the trigger 58. The pair of ribs 80 extend upwardly from an intersection of the first planar surface 68 and the raised wall 76 on opposite sides of the central aperture 64, a small space being provided therebetween.

A series of generally longitudinal raised ribs 82 extend upwardly from the first planar surface 68 of the main section 70 and the nose section 74. A rearward portion 84 of the longitudinal ribs 82 are shorter than a forward portion 86 of the ribs 82 and generally serve to slidably support a portion of the trigger 58. The forward portion 86 of the ribs extend upwardly a greater height from the upper surface 68 than does the raised wall 76, and generally serve to slidably support another portion of the trigger 58 as well as the pawl 60, as will be more fully described hereafter. As illustrated, one of the generally longitudinal ribs 82 has a generally J-shaped portion 87, which guides the straightening cable 36 towards the mounting post 38 provided by the handle 14. Also, two of the ribs define a slot 89 which slidably receives the mounting post 38.

The nose section 74 of the first body section 54 narrows as it extends away from the rectangular main section 70. The nose section provides a shaft-receiving terminal end 90 and a pair of fastener-receiving apertures 92. The shaft-receiving terminal end 90 includes a semi-cylindrical bore 91. The wall surrounding the bore 91 provides a radially inwardly directed projection 94 which is adapted to extend into the crossbore 32 in the proximal end 18 of the shaft 16 and thereby mount the shaft to the handle 14. A semi-circular end wall 93, which defines an end of the bore 91, provides a notch 95 which allows passage of the control cables 34 and 36, the fluid communicating tube 33, and the fiber optic bundle 35 therethrough.

Figure 4:
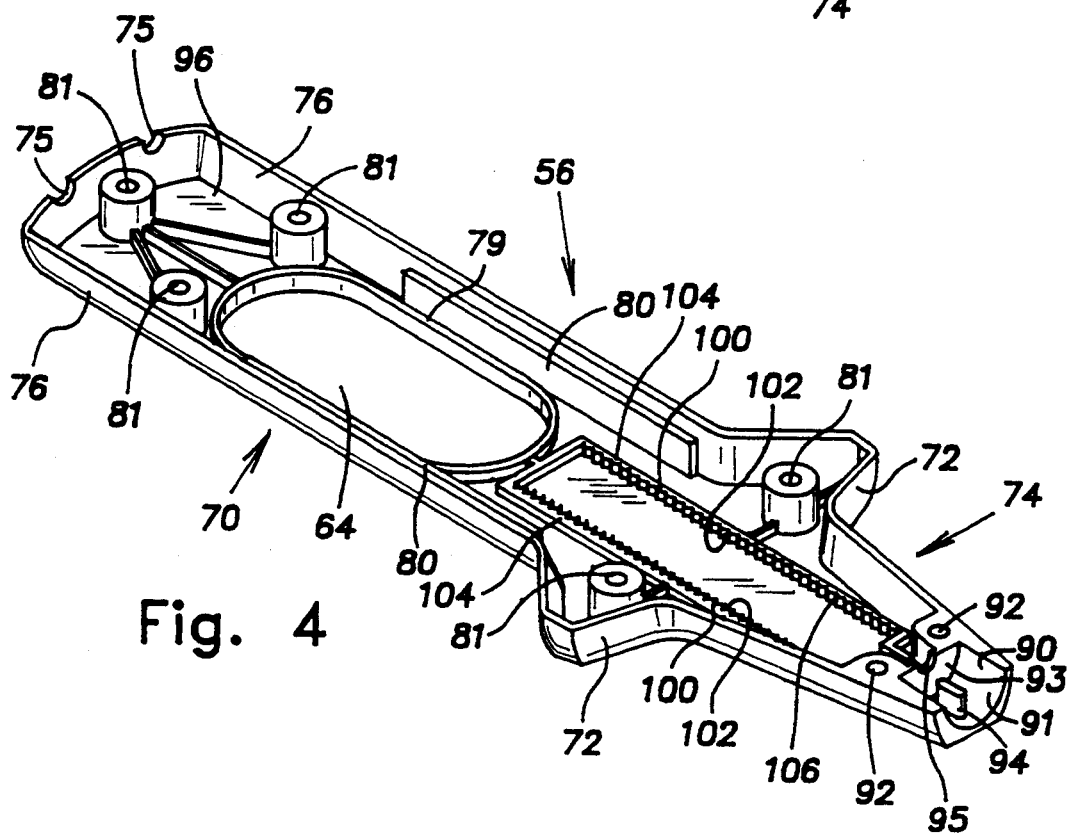
FIG. 4 is a perspective view of the interior of the second body section of the present invention.

In some respects, the second body section 56 of the handle, as shown best in FIGS. 1 and 4, is a mirror image of the above-described first body section 54. Therefore, identical features will be identified with the same reference numerals used in the description of the first body section 54.

The second body section 56 integrally includes a second planar surface 96 which extends between and generally covers a generally rectangular main section 70, a pair of outwardly extending wings 72, and a nose section 74. An outwardly flared raised wall 76 extends from the perimeter of the second planar surface 96, generally surrounding the main section 70, the wings 72 and the nose section 74, as illustrated. As stated previously, the raised wall 76 of the second body section 56 has formed therein a pair of semi-circular notches 75 which cooperate with like notches 73 in the first body section 54 to receive the connectors 77, 78 for the fluid communicating tube 33 and the fiber optic bundle 35.

The main section 70 of the second body section 56 includes a central aperture 64, a pair of raised ribs 80, and a series of raised fastener-receiving bosses 81 which extend out of the second planar surface 96. The central aperture 64 is surrounded by a raised surface 79 which slidably receives an outer end 66 of the trigger 58. The pair of raised ribs 80 extend upwardly from an intersection of the second planar surface 96 and the raised wall 76 on opposite sides of the central aperture 64, a small space being provided therebetween.

The pairs of raised ribs 80 and the raised walls 76 cooperate to define a pair of longitudinal trigger receiving slots 98, which are shown best in FIG. 1. The raised surfaces 79 surrounding the central aperture 64 cooperate to define a slot which slidably receives the trigger 58 and allows the trigger to extend out of the inner chamber defined by the first and second body sections 54 and 56, as will be described more fully hereafter.

The nose section 74 of the second body section narrows as it extends away from the rectangular main section 70, providing a shaft-receiving terminal end 90 and a pair of fastener-receiving apertures 92. The shaft-receiving terminal end 90 includes a semi-cylindrical bore 91 for the receipt of the shaft 16. The wall surrounding the bore 91 includes a radially inwardly directed projection 94 which extends into the crossbore 32 in the proximal end 18 of the shaft 16. A semi-circular end wall 93 of the bore 91 provides a notch 95 which allows passage of the cables 34 and 36, the fluid communicating tube 33, and the fiber optic bundle 35 therethrough.

As will be recognized, when the handle is assembled the bosses 81 and fastener-receiving apertures 92 provided by the second body section 56 are in-line with those provided by the first body section 54 and allow conventional fasteners 99 to interconnect the body sections (FIG. 2), thereby forming a rigid handle structure. Naturally, the first and second handle sections 54, 56 can be attached by any known means, such as adhesives, sonic welding, extrusion welding, or the like, without departing from the scope and spirit of the present invention.

The second planar surface 96 further provides a pair of opposed stationary ratchets 100 which extend between the main section 70 and the nose section 74. The ratchets 100 are engaged by the pawl 60, as will be described hereafter.

The ratchets 100 include generally inwardly directed teeth 102. As shown best in FIGS. 1 and 4, the teeth located on a rear half 104 of the ratchets 100 are directed towards the front of the handle 14 and the teeth located on a front half 106 of the ratchets 100 are directed towards the rear of the handle.

The location and direction of the teeth 102 facilitate engagement and disengagement of the X-shaped pawl 60 therewith. Naturally, the present invention is not limited to the specific size and shape of the ratchets 100 and pawl 60 illustrated herein, the described elements merely being exemplary of the preferred embodiment presently contemplated by the inventor.

As is clear from the foregoing description, the inner chamber is defined by the space between the main rectangular sections 70 and the nose sections 74 of the first and second body sections 54 and 56 when the handle 14 is assembled. The inner chamber slidably receives the trigger 58 and the pawl 60.

Figure 5:
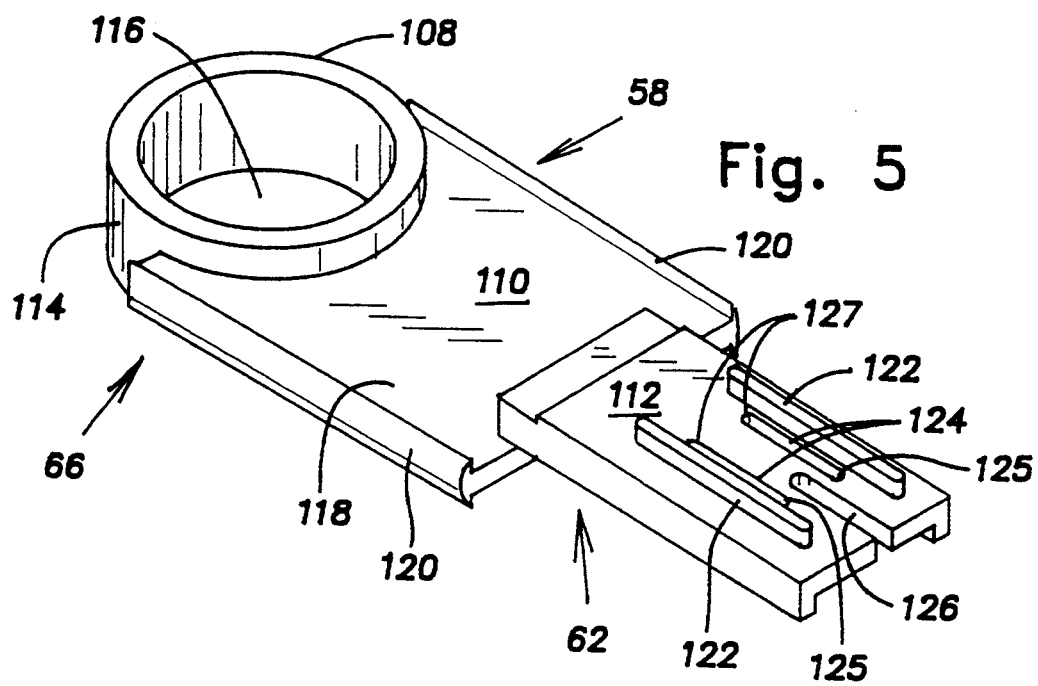
FIG. 5 is a perspective view of the trigger of the present invention.

Turning to FIG. 5, the trigger 58 of the present invention is shown to generally include a ring-shaped end 108, a slide portion 110, and an interconnecting portion 112. The trigger 58 comprises an actuator which is manipulated by the user to move the head 12, via the motion transfer means comprising the cables 34 and 36, between arched and straight configurations.

The ring-shaped end 108 includes a cylindrical portion 114 which defines a circular opening 116 adapted to receive the surgeon's finger. As shown best in FIGS. 1 and 2 and mentioned previously, the ring-shaped end 108 is generally received by the central aperture 64 provided by the handle 14 as well as being slidably received by the perimeter slot defined by the raised surfaces 79 surrounding the central aperture 64. The circular opening 116 is preferably adapted to receive the surgeon's thumb during use of the manipulator, while a pair of the surgeon's fingers are draped over the outwardly extending wings 72.

The slide portion 110, which extends between the ring-shaped end 108 and the interconnecting portion 112, includes a generally planar body 118 and a pair of longitudinally-extending flanges 120. The flanges project above and below the planar body 118, and are adapted to be slidably received by the longitudinal slots 98 formed between the pairs of raised ribs 80 and the raised walls 76 of the handle 14. The planar body 118 of the slide member 110 is slidably supported by the shorter rearward portion 84 of the longitudinal ribs 82.

Receipt of the flanges 120 in the longitudinal slots 98 limits side-to-side movement of the trigger 58 while receipt of the ring-shaped end 108 in the slot between the raised surfaces 79 limits relative up-and-down motion of the trigger 58. Hence, the trigger is generally capable of only longitudinal movement, making the operation thereof smooth and relatively precise.

The interconnecting portion 112 includes a pair of upstanding rails 122, a pair of slotted openings 124, and a notch 126. Adjacent the slotted openings 124 the interconnecting portion 112 includes forward edges 125 and rearward edges 127 which are operable to engage the pawl 60, as will be more fully described hereafter.

The interconnecting portion 112 is slidably supported by the forward portions 86 of the longitudinal ribs 82. The rails 122 of the interconnecting portion are designed to disengage the X-shaped pawl 60 from the ratchets 100 while the slotted openings 124 and the notch 126 are designed to receive portions of the X-shaped pawl 60 and move the pawl along the length of the ratchets 100 within the inner chamber.

Figure 6:
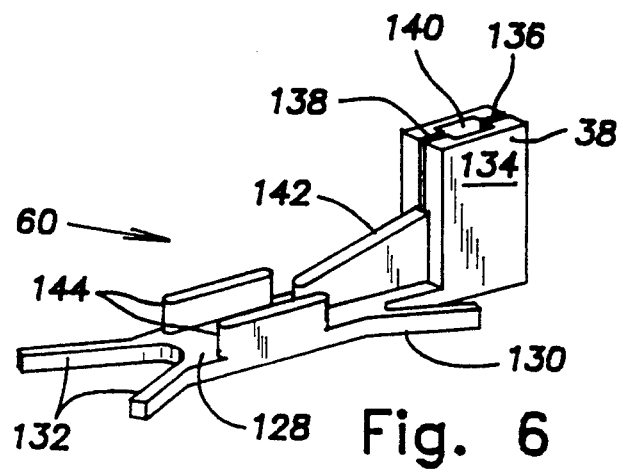
FIG. 6 is a perspective view of the pawl of the present invention.

The pawl 60, as shown best in FIG. 6, includes a central body section 128, a pair of front legs 130, a pair of rear legs 132, and an upstanding section 134.

The upstanding section 134, which serves as the mounting post 38, includes forward and rearward slots 136, 138 and a central rectangular bore 140. The slots 136 and 138 and the bore 140 are adapted to receive and retain the control cables 36 and 34 which are used to manipulate the head 12. More specifically, the central rectangular bore 140 is designed to receive the terminal knobs or balls 44 (FIG. 18) provided by the proximal ends 40 of the cables 34 and 36, while the cables themselves extend through the slots 138 and 136. In the preferred embodiment, the arching cable 34 extends through the rearward slot 138 while the straightening cable 36 extends through the forward slot 136.

The central body section 128 provides an upwardly ramping member 142 and a pair of upstanding slides 144. When assembled, the interconnecting portion 112 of the trigger 58 is generally positioned over the pawl 60 such that the upstanding slides 144 are loosely received by the slotted openings 124, each of the upstanding rails 122 being located between a front and rear leg of the pawl 60 and the upwardly ramping member 142 being received by the notch 126 in the interconnecting portion 112.

The upstanding rails 122 of the trigger 58 are operable to disengage respective paired legs 130, 132 from the ratchets 100. The upstanding slides 144 of the pawl 60 are operable to engage respective edges 125, 127 of the interconnecting portion 112 which surround the slotted openings 124, forcing the pawl 60 and cables 34, 36 to move in accordance with the trigger 58.

Naturally, the upstanding slides 144 of the pawl 60 are rather loosely received by the slotted openings 124 in the trigger 58, allowing the slides 144 to move within the slotted openings 124 prior to engaging the edges 125, 127 therearound. For example, when the trigger 58 is moved rearwardly, the rails 122 disengage the rear legs 132 from the ratchets 100 and, after the trigger has further moved rearwardly a short distance, the forward edges 125 of the trigger surrounding the slotted openings 124 engage the slides 144 and force the pawl 60 to move rearwardly with the trigger. Alternatively, when the trigger 58 is moved forwardly, the rails 122 disengage the front legs 130 from the ratchets 100 and, after the trigger 58 has further moved forwardly a short distance, the rearward edges 127 of the trigger surrounding the slotted openings 124 engage the slides 144 and force the pawl 60 to move forwardly therewith.

The lost motion of the trigger 58 allows the rails 122 to disengage the legs 130, 132 from the ratchets 100 before the slides 144 engage the interconnecting portion 112 surrounding the slotted openings 124. Naturally, it is not possible to move the pawl 60 prior to disengagement of either the front 130 or rear 132 pair of legs from the ratchets 100.

The head 12, as shown best in FIGS. 1 and 2, includes an adaptor link 146, an angle link 148, a tip link 150, and a nose tip 152.

With reference to FIG. 8, the adaptor link 146 is designed to mount within the cylindrical bore 26 provided by the distal end 20 of the shaft 16. To that end, the adaptor link 146 includes a generally tubular body 154 and an enlarged cap 156. The enlarged cap 156 has a diameter generally equal to the diameter of the shaft 16 to provide a smooth transition between the shaft 16 and head 12.

The tubular body 154 is shaped as a hollow cylinder and has two pairs of circular holes 158 in the sidewalls thereof for the receipt of the mounting pins 30. As discussed previously, the mounting pins 30 extend through crossbores 28 provided in the sidewall of the distal end 20 of the shaft 16 and into the holes 158 provided by the tubular body 154 to attach the head 12 to the shaft 16. A longitudinal bore 159 extends the length of the tubular body 154 and the enlarged cap 156. As illustrated, the tubular body 154 generally merges with an proximal end 160 of the enlarged cap 156.

As shown best in FIGS. 9 and 10, the enlarged cap 156 is generally shaped as a cylinder having a longitudinally-directed rectangular outer bore 162 and a pair of smaller inner bores 164. The inner bores 164 overlap edges of the longitudinal bore 159 and extend into the enlarged cap 156 a short distance, as illustrated. The inner bores 164 are on radially opposite sides of the longitudinal bore 159, and serve as individual paths for the control cables 34 and 36, as well as paths for the fluid communicating tube 33 and the fiber optic bundle 35.

A distal end 166 of the enlarged cap has extending outwardly therefrom a pair of arms 168, each of which include a hinge pin receiving aperture 170 to allow mounting of the angle link 148 thereto. A sidewall of the outer bore 162 serves as a stop surface to limit the angular range of pivot of the angle link 148 relative to the adaptor link 146.

The angle link 148, as illustrated in FIGS. 11-13, has a generally cylindrical main body section 174. The main body section 174 defines first and second coaxial longitudinal bores 176 and 178 which extend inwardly a short distance from proximal and distal ends 180 and 182 thereof, respectively. The main body 174 further defines first and second holes 184 and 186 which extend from radially opposite corners of the first bore 176 to radially opposite corners of the second bore 178. As illustrated, the first hole 184 extends from one lower corner of the first bore 176 to an opposite lower corner of the second bore 178. Likewise, the second hole 186 extends from one upper corner of the first bore 176 to an opposite upper corner of the second bore 178.

Each of the first and second holes 184 and 186 are formed by a pair of parallel, overlapping, diagonally-directed bores, as shown best in FIG. 13. The first and second coaxial bores 176 and 178 and first and second holes 184 and 186 are designed to carry the cables 34 and 36, the fluid communicating tube 33, and the fiber optic bundle 35. Preferably, the arching cable 34 is inserted through the first hole 184 while the straightening cable 36 is inserted through the second hole 186.

Both ends of the angle link 148 include a pair of outwardly extending arms 196. The arms 196 include a generally curved terminal end, having an outwardly extending projection 198 emanating therefrom. The projection 198 is designed to engage stop surfaces provided by the tip link 150 and adaptor link 146 to limit the angular range of pivot of the angle link 148 relative thereto. The arms 196 further include outwardly directed cylindrical extensions 200 which serve as hinge pins to allow the angle link 148 to pivotally attach to the adaptor link 146 and the tip link 150.

Figure 14:
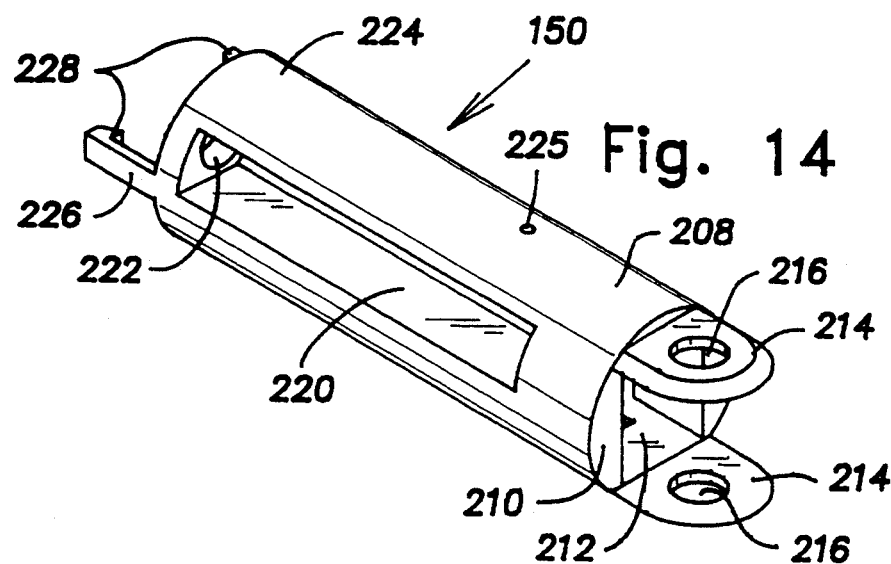
FIG. 14 is a perspective view of the head tip link of the present invention.
Figure 15:
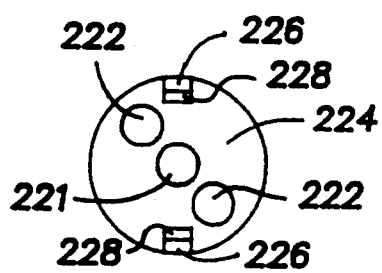
FIG. 15 is a side elevational view of the distal end of the head tip link of the present invention.
Figure 16:
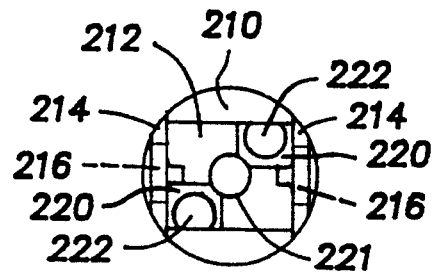
FIG. 16 is a side elevational view of the proximal end of the head tip link of the present invention.

The tip link 150, which is shown best in FIGS. 14-16, serves as the terminal link of the head 12 and includes a cylindrical body section 208. At a proximal end 210 of the tip link 150 there is provided an inwardly directed rectangular hole 212 and a pair of outwardly extending arms 214. A sidewall surrounding the hole 212 serves as a stop surface to limit the angular range of pivot of the angle link 148 relative to the tip link 150. The arms 214, which are generally identical to those provided by the adaptor link 146, each provide a hinge pin receiving hole 216.

A bottom of the rectangular hole 212 has projecting therefrom a pair of longitudinally-directed slotted openings 220 and a circular hole 221, as shown best in FIG. 16. The slotted openings 220 are radially opposite one another relative to the axis of the cylindrical body section 208 and align with the first and second holes 184, 186 of the angle link 148. The slotted openings 220 extend through the sidewall of the tip link 150, and are designed to accept the turnbuckles 46 which are attached to distal ends 42 of the cables 34, 36, as discussed previously. The circular hole 221 is provided to carry the fluid communicating tube 33 and the fiber optic bundle 35.

A pair of radially opposed holes 222 extend inwardly from a distal end 224 of the tip link 150 and project into the slotted openings 220, providing access to the tensioning screw receiving end 50 of the turnbuckles 46 after they are inserted therein. The circular hole 221 projects out of the distal end 224 of the tip link 150. A crossbore 225, which is provided to allow the fluid communicating tube 33 to communicate with an expandable balloon 227 (FIG. 1) carried by the tip link 150, intersects with and extends into the circular hole 221. The balloon 227, which is preferably made out of PTFE and has an expanded diameter of about 19mm, is mounted to the exterior of the sheath 21 at the tip link 150 and is operable to enlarge or inflate and provide better traction with the tissue defining the lumen, as will be described more fully hereafter.

The distal end of the tip link 150 further includes a pair of bayonet arms 226 which are designed to elastically receive the nose tip 152. The bayonet arms 226 include terminal hook-shaped ends 228.

Figure 17:
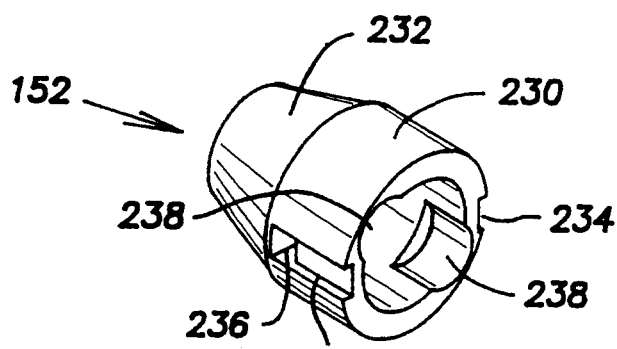
FIG. 17 is a perspective view of the head nose tip of the present invention.

The nose tip 152 is illustrated in FIG. 17 and includes a generally cylindrical portion 230 which merges into a terminal frustoconical portion 232. A pair of notched grooves 234 are provided in the exterior of the cylindrical section 230 while a pair of apertures 236 (one shown) extend through the sidewall of the nose tip 152 at a terminal end of the grooves 234 to allow mounting of the nose tip 152 to the tip link 150. The terminal hooked ends 228 of the bayonet arms 226 are received by the pair of apertures 236, allowing the arms 226 to fit within the notched grooves 234 and be generally flush with the outer surface of the nose tip 152.

A pair of semi-cylindrical notches 238 are provided on the interior of the nose tip 152 to receive the heads of the turnbuckle-retaining screws 52. As is well known in the art, the screws 52 may be rotated to axially move the turnbuckle 46 relative to the tip link 150 and thereby tension the respective cable attached to the opposite end thereof.

The nose tip 152 further includes an end cap 240 which is press fit into a distal end thereof, as shown best in FIG. 1. The end cap 240 provides a mounting bore 242 to which the fiber optic bundle 35 terminally attaches, allowing visualization of the area in front of the head 12.

It should be noted that the nose tip 152, the end cap 240, or any of the component links of the head 12, can be formed of a transparent material to allow an additional light source (not shown) to be mounted therein. Additional illumination of the area towards the front of the head 12 augments the light supplied via the fiber optic bundle 35. Moreover, by providing an additional light source, the location the head within the patient's body may be observed through the patient's body. This is useful, for example, in esophageal procedures wherein it is possible to view the light source from an exterior of the body, thereby allowing a more precise positioning of the device within the esophagus prior to manipulation thereof. Naturally, the light source can be either battery powered or can be supplied power via an electrical cable (not shown) threaded through one of the lumens 22 provided by the shaft 16.

Assembly of the intraluminal manipulator 10 will be described hereafter with reference to the foregoing description and drawing figures.

The head 12 is preliminarily assembled by slipping the turnbuckles 46 into the slotted openings 220 in the tip link 150 and threading the associated cables 34 and 36 through the rectangular hole 212. Thereafter, the cables 34 and 36 are threaded through the first and second holes 184 and 186 of the angle link 148. Preferably, as stated previously, the arching cable 34 extends through the first hole 184 while the straightening cable 36 extends through the second hole 186.

The fiber optic bundle 35 is threaded through the mounting bore 242 in the end cap 240 and through the hole 221 in the tip link 150. The end of the fiber optic bundle 35 is attached or connected to the end cap 240 to prevent the removal of the bundle 35 therefrom. The fluid communicating tube 33 is threaded through the crossbore 225 in the tip link 150 and into the hole 221, eventually exiting at the proximal end 210 of the tip link. Thereafter, the fluid communicating tube 33 and the fiber optic bundle 35 are threaded through the first and second holes 184, 186 of the angle link 148, respectively.

The arms 214 of tip link 150 are pivotally mounted onto the arms 198 at the distal end 182 of the angle link 148 such that the cylindrical extensions 200 which serve as hinge pins extend into the hinge pin receiving holes 216.

With the tip link 150 and angle link 148 so assembled, the cables 34 and 36, the fluid communicating tube 33, and the fiber optic bundle 35 are threaded through the inner bores 164 and longitudinal bore 159 of the adaptor link 146. Then, the adaptor link 146 is pivotally mounted to the angle link 148. Mounting is accomplished by snapping the cylindrical extensions 200 provided by the arms 198 at the proximal end 180 of the angle link 148 into the hinge pin receiving holes 170 provided by the arms 168 of the adaptor link 146. With this done, the main movable components of the head 12 are assembled and ready to be mounted to the shaft 16.

Prior to mounting of the head 12 to the shaft 16, the cables 34 and 36, the fluid communicating tube 33, and the fiber optic bundle 35 are threaded through individual lumens 22 and pulled out the proximal end 18 of the shaft 16. The tubular body 154 of the adaptor link 146 is then pushed into the cylindrical bore 26 provided in the distal end 20 until the proximal end 160 of the enlarged cap 156 engages the shaft 16.

Thereafter, the flexible elastomeric sheath 21, which may include lubrication on the interior surface thereof, is slidably placed over the head 12 and shaft 16. Holes are punched in the sheath 21 in alignment with the various holes 28, 32,225 provided by the shaft 16 and head 12. An end of the sheath 21 is then attached by adhesives or the like to the distal end 224 of the tip link 150 while an opposite end of the sheath is similarly attached to the proximal end 18 of the shaft 16. Thereafter, the fluid communicating tube 33, which extends out of the hole 225 in the tip link 150 and the newly-formed hole in the sheath 21, is fastenably secured to the sheath 21 and the tip link 150, thereby preventing removal of the tube 33 from the hole 225.

The crossbores 28 provided by the distal end 20 of the shaft 16 and the holes 158 provided by the tubular body 154 are aligned and mounting pins 30 inserted therethrough, positively attaching the movable components of the head to the shaft.

The shaft 16 is attached to the second body section 56 of the handle by placing the proximal end 18 of the shaft 16 over the shaft receiving terminal end 90 of the nose section 74 such that the radially inwardly directed projection 94 provided thereby extends into the crossbore 32. The cables 34 and 36, the tube 33, and the bundle 35 are placed into the notch 95 provided by the semi-circular wall 93 of the nose section 74.

The handle 14 is assembled by placing the pawl 60 between the ratchets 100 of the second body section 56 such that the pair of rear legs 132 engage teeth 102 on the rear half 104 of the ratchets 100 and the pair of front legs 130 engage teeth 102 on the front half 106 of the ratchets 100. Preferably, the pawl 60 is placed toward the front of the ratchets 100 to ease attachment of the cables 34 and 36. The upstanding section 134 extends upwardly from the combined pawl 60 and second body section 56.

The trigger 58 is placed over the pawl 60 and second body section 56. The pair of slotted openings 124 of the trigger loosely receive the pair of upstanding slides. 144 provided by the central body section 128 of the pawl 60. Each of the upstanding rails 122 of the trigger fit between the front and rear legs 130, 132 on opposite sides of the central body section 128 of the pawl. The upwardly ramping member is received by the notch 126 in the interconnecting portion 112 of the trigger. The longitudinal flanges 120 of the slide member 110 fit into the longitudinal slots 98 between the raised ribs 80 and the outwardly flared raised wall 76 provided by the second body section 56. Also, the cylindrical member 114 of the trigger is slidably supported by the raised surface 79 surrounding the central aperture 64.

With the trigger 58 and X-shaped pawl 60 mounted in the second body section 56, the cables 34 and 36, the fluid communicating tube 33, the fiber optic bundle 35, and first body section 54 can be attached thereto. Connectors 77, 78 are attached to the ends of the fluid communicating tube 33 and the fiber optic bundle 35, respectively, and thereafter placed within the semi-circular notches 75 in the raised wall 76 of the second body section 56 such that the annular surfaces 83 of the connectors 77, 78 are on opposite sides of the wall 76.

The terminal ball 44 at the proximal end 40 of straightening cable 36 is inserted into the rectangular bore 140 in the upstanding section 134 of the X-shaped pawl 60. The straightening cable 36 extends through the forward slot 136 in the upstanding section 134 towards the shaft 16. Thereafter, the trigger 58 and X-shaped pawl 60 are moved rearwardly to tension the straightening cable 36 and allow attachment of the arching cable 34 to the pawl 60.

The arching cable 34 is thereafter wrapped around the rib with the J-shaped portion 87 and the terminal knob 44 of the cable 34 is inserted into the rectangular hole 140 in the upstanding section 134. The arching cable 34 is received by the rearward slot 138. The first body section 54 is then placed on the second body section 56 and the two sections are secured by conventional fasteners 99 which engage the fastener receiving bosses 81 and apertures 92. Alternatively, the two sections 54, 56 can be secured by sonic welding, extrusion welding, or the like.

As so assembled, the slide member 110 and interconnecting portion 112 of the trigger 58 are slidably received by the rearward portion 84 and forward portion 86 of the longitudinal raised ribs, respectively. The longitudinal flanges 120 of the slide member 110 are received by the slots 98 formed between the outwardly flared raised wall 76 and the raised ribs 80. The ring shaped end 108 of the trigger 58 is slidably received by the slot defined by the raised surfaces 79 surrounding the central aperture 64. The connectors 77, 78 are received by the notches 73, 75 formed in the raised walls 76 of the first and second body sections 54, 56 such that the raised annular surfaces 83 are on opposite sides of the walls 76, preventing removal of the connectors 77, 78 from the handle 14. The upstanding section 134 is slidably received by the slot 89 formed by two of the raised ribs 82. Naturally, the radially inwardly extending projections 94 of the first and second body sections 54, 56 extend into the crossbore 32 in the proximal end 18 of the shaft 16, thereby positively connecting the handle 14 to the shaft.

Final assembly of the head 12 can now commence. The screws 52 are threadably inserted into the tensioning screw receiving ends 50 of the turnbuckles 46, and the longitudinal position of the turnbuckles in the head adjusted. Preferably, the turnbuckles 46 positions are set so that the arching cable 34 fully arches the head 12 when the trigger is in a forwardmost position (FIG. 1) and the straightening cable 36 fully straightens the head 12 when the trigger 58 is in a rearwardmost position. Intermediate the fully-arched and fully-straight positions, the head 12 moves proportionally to the movement of the trigger 58.

Thereafter, the nose tip 152 is snap-fit onto the distal end 224 of the tip link 150, the terminal hooked ends 228 of the bayonet arms 226 being received by the apertures 236 while the arms themselves are received by the grooves 234. The end cap 240, which has the fiber optic bundle 35 attached thereto to allow the remote visualization of the area in front of the head, is press-fit into the end of the nose tip 152.

The balloon 227 is attached by adhesives or the like to the portion of the sheath 21 covering the tip link 150. The balloon 227, which is generally cylindrical in its unexpanded state, generally extends the length of the tip link 150. The annular ends of the balloon 227 are bonded or otherwise adhered to the sheath 21. Therefore, an inflation chamber is formed between the exterior surface of the sheath 21 and the interior surface of the balloon 227. As is clear from FIG. 1, the fluid communicating tube 33 communicates with the inflation chamber, allowing pressurized fluid to expand the balloon 227.

Operation of the intraluminal manipulator 10 for use in manipulating a patient's esophagus will hereafter be described with reference to the foregoing description and drawing figures.

The manipulator 10, with the head 12 initially in the fully straight position (i.e.—trigger in the rearwardmost position) is inserted into a patient's esophagus the desired amount. The position of the head 12 is viewed via the fiber optic bundle 35 and the fiberscope (not shown). Alternatively, the head position can be determined through use of an independent internal light source, as discussed previously.

The trigger 58 is pushed forwardly by the surgeon, causing the upstanding rails 122 to disengage the front legs 130 of the X-shaped pawl 60 from the ratchets 100. After the trigger moves forwardly a short distance, the upstanding slides 144 of the pawl 60 are engaged by the rearward edges 127 surrounding the slotted openings 124 of the trigger 58, causing the pawl 60 to move relatively forwardly with the trigger 58.

Forward motion of the X-shaped pawl 60 causes the arching and straightening cables 34 and 36, each of which have proximal ends 40 received by the upstanding section 134 of the X-shaped pawl 60, to tension and slacken, respectively. Tensioning of the arching cable 34 causes the distal end 42 of the arching cable to move towards the handle. This results in the angle link 148 pivoting clockwise relative to the adaptor and tip links 146, 150 about the axes defined by the cylindrical extensions 200 which outwardly project from the arms 196.

When the head 12 firmly engages the interior of the patient's esophagus, the surgeon can release the trigger, allowing the X-shaped pawl 60 to engage the ratchet 100 and thereby maintain the cables 34, 36 in position and, hence, the head configuration. Thereafter, the handle 14 and shaft 16 can be pulled, rotated and twisted, or otherwise re-oriented to correspondingly reposition the patient's esophagus. The handle and shaft, once placed in the proper position to orient the esophagus as desired, can be manually held to maintain the esophagus in the desired position.

When the procedure is completed, the trigger 58 is pulled back, causing the upstanding rails 122 to disengage the rear legs 132 of the X-shaped pawl 60 from the ratchets 100. After the trigger moves rearwardly a short distance, the upstanding slides 144 of the pawl 60 are engaged by the forward edges 125 surrounding the slotted openings 124 of the trigger, causing the pawl 60 to move rearwardly with the trigger 58.

Rearward movement of the pawl 60 causes the arching and straightening cables 34, 36, which have proximal ends 40 received by the upstanding section 134 of the pawl 60, to slacken and tension, respectively. Tensioning of the straightening cable 36 causes the distal end 42 of the straightening cable to move towards the handle 14, forcing the angle link 148 to pivot counterclockwise relative to the adaptor and tip links 146, 150. This results in the head moving from the arched configuration to the less-arched or straight configuration. When the head is in the straight configuration (i.e. with the adaptor, angle and tip links 146, 148 and 150 in a generally coaxial arrangement) the head can be removed from the patient's esophagus.

Alternatively, or when the arching of the head 12 alone is insufficient to frictionally engage the esophagus, the expandable balloon 227 can be deployed. With the stop cock 85 open, pressurized fluid is introduced into the balloon 227 via the fluid communicating tube 33, expanding the balloon and causing it to engage the esophagus. When the desired expansion of the balloon 227 has been reached, the stop cock 85 is closed, and the pressure source (not shown) is removed from the connector 77. Following the procedure, fluid is released from the balloon 227 by opening the stop cock 85 and allowing the fluid to drain out naturally or under the influence of suction.

It is important to realize that although the intraluminal manipulator has been described in relation to its use in manipulating a patient's esophagus, its intended field of use is not so limited. Rather, the intraluminal manipulator is adapted to extend into and reorient a lumen defined and provided by any tissue. This tissue may be the patient's esophagus, but could also be the colon or any other tubular organ. Moreover, it must be noted that it is not necessary for the lumen to have an exterior opening because access thereto can be gained by inserting a trocar laparoscope to the site, incising a tract through the lumen-defining tissue and inserting the manipulator through the incised tract into the lumen. Such a procedure would be especially practical in manipulation and reorientation of the large and small intestine, and various other tissues wherein the natural orifice is too remote from the area to be manipulated.

It is the nature of the present invention to encourage and facilitate the inclusion of additional features or modifications to meet the specific requirements of any particular application. For example, the expandable balloon 227 can be configured, formed, or attached in many ways equivalent to the one specifically set forth herein. Also, the manner in which the sheath 21 is mounted on the shaft 16 and head 12 is capable of various modifications without departing from the scope and spirit of the present invention.

Therefore, while the preferred embodiment of the present invention is shown and described herein, it is to be understood that the same is not so limited but shall cover and include any and all modifications thereof which fall within the purview of the invention as defined by the claims appended hereto.

We claim:

1. An intraluminal manipulator comprising a head, a handle and a motion transfer means connecting said head to said handle, said head being movable between generally straight and generally arched configurations, said handle housing an actuation means, said motion transfer means being operable to transfer motion from the actuation means to the head, whereby manipulation of the actuation means in a first manner causes the head to arch and manipulation of the actuation means in a second manner causes the head to straighten, the head being adapted to be inserted into a lumen while in a generally straight configuration and the actuation means thereafter being manipulated in said first manner, causing the head to arch, said head being adapted to engage a surface surrounding the lumen when in said arched configuration, the actuation means being manipulated in the second manner to straighten the head, disengaging the head from the surface surrounding the lumen and thereby allowing removal of said head from the lumen and wherein a shaft interconnects the handle and the head, said shaft having a plurality of inner longitudinal channels formed therethrough which provide a communication path between the handle and the head from the motion transfer means, said actuation means comprising a trigger, said handle comprises first and second body sections, said first and second body sections defining an inner chamber and a central aperture, said trigger having an inner end which is received by the inner chamber and an outer end which extends into the central aperture and wherein the second body section comprises a pair of ratchets, said ratchets having front and rear portions, said front portion including teeth which point in a first direction and said rear portion including teeth which point in a second direction.

2. An intraluminal manipulator according to claim 1, wherein the motion transfer means comprises arching and straightening cables, each of said cables extending between said head and said handle via individual ones of said longitudinal channels provided within the shaft.

3. An intraluminal manipulator according to claim 2, wherein said trigger comprises a sliding trigger.

4. An intraluminal manipulator according to claim 1, wherein the head comprises a plurality of articulated links.

5. An intraluminal manipulator according to claim 1, further comprising an X-shaped pawl, said X-shaped pawl having a pair of rear legs which engage the rear portions of said ratchets and a pair of front legs which engage said front portions of said ratchets.

6. An intraluminal manipulator according to claim 5, wherein the X-shaped pawl further includes a cable receiving means, said cable receiving means being adapted to receive a proximal end of said cables and prevent the removal of the cables from the handle.

7. An intraluminal manipulator according to claim 6, wherein the X-shaped pawl includes a slide and the inner end of the trigger includes a pair of rails and a slot, the slide of the X-shaped pawl being received by the slot and each of the rails being located between one of the pair of front legs and one of the pair of rear legs, whereby rearwardly directed movement of the trigger causes the rails to disengage the rear pair of legs from the ratchets and causes the slide to engage a first edge of the slot and thereby cause the X-shaped pawl to move rearwardly with the trigger and forwardly directed movement of the trigger causes the rails to disengage the front pair of legs from the ratchets and causes the slide to engage a second edge of the slot and thereby cause the X-shaped pawl to move forwardly with the trigger.

8. An intraluminal manipulator according to claim 7, wherein forwardly directed movement of the trigger causes the head to arch and rearwardly directed movement of the trigger causes the head to straighten.

9. An intraluminal manipulator as in claim 8, wherein at least a portion of the head and shaft are covered by a flexible sheath.

10. An intraluminal manipulator as in claim 1, wherein the head further comprises an expandable member, said expandable member being operable to expand and frictionally engage the surface surrounding the lumen.

11. An intraluminal manipulator as in claim 1, further comprising a means to allow remote visualization of a portion of the lumen adjacent the head, said means including a fiber optic bundle.

12. An intraluminal manipulator comprising a head, a shaft, a handle, and a control means, said shaft providing a communication path between said head and said handle, said head comprising a plurality of articulated links, said links being movable by the control means to move said head between generally straight and generally arched configurations, said handle including a trigger and a pawl, said control means being attached to said pawl and said pawl and said control means capable of articulating with respect to said trigger so as to control motion of said links, said trigger engaging the pawl and being operable to move the pawl and the control means therewith, said control means comprising a pair of cables, said cables extending between the handle and the had via the communication path defined by the shaft and being operable to arch the head when the trigger is moved in a first direction and to straighten the head when the trigger is moved in a second direction.

13. An intraluminal manipulator according to claim 12, wherein the handle further comprises first and second body sections, said trigger and pawl begin received by a space defined by said first and second body sections.

14. An intraluminal manipulator according to claim 13, wherein the second body section includes at least one ratchet, said pawl engaging the ratchet and thereby maintaining the configuration of the links comprising the head.

15. An intraluminal manipulator according to claim 13, wherein said second body section provides a pair of ratchets and the pawl is an X-shaped pawl having a pair of rear legs and a pair of front legs, said rear legs engaging a rear portion of said ratchets and said front legs engaging a front portion of said ratchets.

16. An intraluminal manipulator according to claim 15, wherein the cables are received by the X-shaped.

17. An intraluminal manipulator according to claim 16, wherein the X-shaped pawl includes a slide and an inner end of the trigger includes a pair of rails and a slot, the slide of the X-shaped pawl being received by the slot and each of the rails being located between one of the pair of front legs and one of the pair of rear legs, whereby rearwardly directed movement of the trigger causes the rails to disengage the rear pair of legs from the ratchets and causes the slide to engage a first edge of the slot and thereby cause the pawl to move rearwardly with the trigger and forwardly directed movement of the trigger causes the rails to disengage the front pair of legs from the ratchets and causes the slide to engage a second edge of the slot and thereby cause the X-shaped pawl to move forwardly with the trigger.

18. An intraluminal manipulator according to claim 17, wherein forwardly directed movement of the trigger causes the head to arch and rearwardly directed movement of the trigger causes the head to straighten.

19. An intraluminal manipulator as in claim 18, wherein at least a portion of the head and shaft are covered by a flexible sheath.

20. An intraluminal manipulator as in claim 12, wherein the head further comprises an expandable member, said expandable member being operable to expand and frictionally engage a surface surrounding a lumen into which the head is placed.

21. An intraluminal manipulator as in claim 12, further comprising a means to allow remote visualization of a portion of a lumen in which the head is placed, said means including a fiber optic bundle.

22. An intraluminal manipulator, comprising:
a head, said head including a plurality of articulated links which are movable between a generally straight configuration and a generally arched configuration;
a control means, said control means comprising an arching and a straightening cable, each of said cables having a distal end attached to the head;
a handle, said handle comprising first and second body sections which cooperate to define a central aperture and an inner chamber, a trigger, and an X-shaped pawl, said first body section providing a series of generally longitudinal ribs which slidably support the trigger and pawl, said second body section including a pair of ratchets which are adapted to hold said X-shaped pawl in position relative thereto, said trigger including an outer end which extends into the central aperture and an inner end which is received by the inner chamber, said inner end including a pair of upstanding rails and a pair of slots, said X-shaped pawl including an upstanding section, a pair of upstanding slides, a pair of rear legs and a pair of front legs, said upstanding section being adapted to receive and retain a proximal end of each cable, said front and rear legs engaging one of said ratchets, each of the upstanding slides extending into one of the slots and each of the rails extending between one of the front legs and one of the rear legs, said rails being operable to disengage the pair of rear legs when the trigger is moved rearwardly and the pair of front legs when the trigger is moved forwardly while the slides engage an edge of said slot to move the pawl in unison with the trigger, wherein movement of the trigger in a rearward direction causes the straightening cable to pull the head into a straightened configuration and movement of the trigger in a forward direction causes the arching cable to pull the head into an arched configuration.

23. An intraluminal manipulator as in claim 22, wherein the head further comprises an expandable member, said expandable member being operable to expand and frictionally engage a surface surrounding a lumen into which the head is placed.

24. An intraluminal manipulator as in claim 23, further comprising a means to allow remote visualization of a portion of the lumen adjacent the head, said means including a fiber optic bundle.

25. An intraluminal manipulator according to claim 24, further comprising a shaft, said shaft having a proximal end attached to the handle and a distal end attached to the head, said shaft providing a plurality of longitudinal channels, one of said channels receiving the arching cable and another of said channels receiving said straightening cable.

26. An intraluminal manipulator according to claim 25, wherein one of said links provides a stop surface and another of said links engages said stop surface, the angular range of pivot of the other of said links relative to the one of said links being limited thereby.

27. An intraluminal manipulator according to claim 26, wherein each of said cables include a turnbuckle at said distal end thereof, said turnbuckles being received by one of said links and being operable to tension said cables.

28. An intraluminal manipulator according to claim 27, wherein at least a portion of the head and shaft are covered by a flexible sheath.

* * * * *